(12) United States Patent
Gundlach et al.

(10) Patent No.: US 11,959,133 B2
(45) Date of Patent: Apr. 16, 2024

(54) METHODS AND COMPOSITIONS FOR GENERATING REFERENCE MAPS FOR NANOPORE-BASED POLYMER ANALYSIS

(71) Applicant: University of Washington through its Center for Commercialization, Seattle, WA (US)

(72) Inventors: Jens Gundlach, Seattle, WA (US); Ian M. Derrington, Seattle, WA (US); Andrew Laszlo, Seattle, WA (US); Elizabeth Manrao, Seattle, WA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 688 days.

(21) Appl. No.: 16/824,186

(22) Filed: Mar. 19, 2020

(65) Prior Publication Data
US 2020/0377936 A1 Dec. 3, 2020

Related U.S. Application Data (63) Continuation of application No. 14/395,793, filed as application No. PCT/US2013/037454 on Apr. 19, 2013, now Pat. No. 10,612,083.

(Continued)

(51) Int. Cl.
*C12Q 1/6869* (2018.01)
*G01N 27/447* (2006.01)
*G01N 33/487* (2006.01)

(52) U.S. Cl.
CPC ......... *C12Q 1/6869* (2013.01); *G01N 27/447* (2013.01); *G01N 33/48721* (2013.01)

(58) Field of Classification Search
None
See application file for complete search history.

(56) References Cited

U.S. PATENT DOCUMENTS

| 4,839,265 A | 6/1989 | Ohno et al. |
| 5,486,616 A | 1/1996 | Waggoner et al. |

(Continued)

FOREIGN PATENT DOCUMENTS

| EP | 1956367 A1 | 8/2008 |
| WO | 2007/020457 A2 | 2/2007 |

(Continued)

OTHER PUBLICATIONS

Bashir, A., et al., "A Hybrid Approach for the Automated Finishing of Bacterial Genomes," Nature Biotechnology 30(7):701-707, Jul. 2012.

(Continued)

*Primary Examiner* — J. Christopher Ball
(74) *Attorney, Agent, or Firm* — Christensen O'Connor Johnson Kindness PLLC (57) ABSTRACT

The present disclosure generally relates to the methods and compositions to efficiently analyze polymer characteristics using nanopore-based assays. Specifically disclosed is a method for generating reference signals for polymer analysis in a nanopore system, wherein the nanopore system has a multi-subunit output signal resolution. The method comprises translocating a reference sequence through a nanopore to generate a plurality of reference output signals, wherein each possible multi-subunit sequence that can determine an output signal appears only once in the reference sequence. The output signals are compiled into a reference map for nanopore analysis of an analyte polymer. Also provided are methods and compositions for calibrating the nanopore system for optimized polymer analysis.

12 Claims, 3 Drawing Sheets
Specification includes a Sequence Listing.

Related U.S. Application Data (60) Provisional application No. 61/635,768, filed on Apr. 19, 2012.

(56) References Cited

U.S. PATENT DOCUMENTS

| | | | |
|---|---|---|---|
| 6,002,003 | A | 12/1999 | Shen et al. |
| 6,428,959 | B1* | 8/2002 | Deamer .......... G01N 33/48721 436/151 |
| 7,258,838 | B2 | 8/2007 | Li |
| 2003/0099951 | A1 | 5/2003 | Akeson |
| 2010/0112584 | A1 | 5/2010 | Shao et al. |
| 2010/0143955 | A1 | 6/2010 | Baohua et al. |
| 2010/0291548 | A1* | 11/2010 | Sharaf .................. C12Q 1/6876 435/6.18 |
| 2010/0331194 | A1 | 12/2010 | Turner |
| 2012/0055792 | A1 | 3/2012 | Gundlach |

FOREIGN PATENT DOCUMENTS

| | | |
|---|---|---|
| WO | 2008/124107 A1 | 10/2008 |
| WO | 2011/106459 A2 | 9/2011 |
| WO | 2013/041117 A1 | 3/2013 |
| WO | 2014/135221 A1 | 9/2014 |
| WO | 2015/170102 A1 | 11/2015 |

OTHER PUBLICATIONS

Benner, S., et al., "Sequence-Specific Detection of Individual DNA Polymerase Complexes in Real Time Using a Nanopore," Nature Nanotechnology 2(11):718-724, Nov. 2007.

Betton, J.-M., "Rapid Translation System (RTS): A Promising Alternative for Recombinant Protein Production," Current Protein and Peptide Science 4(1):73-80, Feb. 2003.

Bhattacharya, S., et al., "Molecular Dynamics Study of MspA Arginine Mutants Predicts Slow DNA Translocations and Ion Current Blockades Indicative of DNA Sequence," ACS Nano 6(8):6960-6968, Aug. 2012. (Author manuscript PMCID: PMC3448955, available in PMC Aug. 28, 2012, 15 pages.).

Blanco, L., and M. Salas, "Relating Structure to Function in φ29 DNA Polymerase," Journal of Biological Chemistry 271(15):8509-8512, Apr. 1996.

Blanco, L., et al., "Highly Efficient DNA Synthesis by Phage φ29 DNA Polymerase," Journal of Biological Chemistry 264(15):8935-8940, May 1989.

Branton, D., et al., "The Potential and Challenges of Nanopore Sequencing," Nature Biotechnology 26(10):1146-1153, Oct. 2008.

Butler, T.Z., et al., "Single-Molecule DNA Detection With an Engineered MspA Protein Nanopore," Proceedings of the National Academy of Sciences of the USA (PNAS) 105(52):20647-20652, Dec. 2008.

Chang, S., et al., "Electronic Signatures of All Four DNA Nucleosides in a Tunneling Gap," Nano Letters 10(3):1070-1075, Mar. 2010.

Cherf, G.M., et al., "Automated Forward and Reverse Ratcheting of DNA in a Nanopore at Five Angstrom Precision," Nature Biotechnology 30(4):344-348, Feb. 2012. (Author manuscript PMCID: PMC3408072, available in PMC Oct. 1, 2012, 14 pages.).

Compeau, P.E.C., et al., "How to Apply de Bruijn Graphs to Genome Assembly," Nature Biotechnology 29(11):987-991, Nov. 2011.

Dahl, J.M., et al., "Direct Observation of Translocation in Individual DNA Polymerase Complexes," Journal of Biological Chemistry 287(16):13407-13421, Apr. 2012.

De Vega, M., et al., "Primer-Terminus Stabilization at the 3'-5' Exonuclease Active Site of φ29 DNA Polymerase. Involvement of Two Amino Acid Residues Highly Conserved in Proofreading DNA Polymerases," EMBO Journal 15(5):1182-1192, Mar. 1996.

De Zoysa, R.S.S., et al., "Slowing DNA Translocation Through Nanopores Using a Solution Containing Organic Salts," Journal of Physical Chemistry B 40(113):13332-13336, Oct. 2009.

Derrington, I.M., et al., "Nanopore DNA Sequencing With MspA," Proceedings of the National Academy of Sciences USA (PNAS) 107(37):16060-16065, Sep. 2010.

Durbin, R., et al., "Biological Sequence Analysis," 11th ed., Cambridge University Press, Cambridge, U.K., 2006, pp. 92-96.

Evans, D.A., et al., "The Asymmetric Synthesis of α-Amino Acids. Electrophilic Azidation of Chiral Imide Enolates, a Practical Approach to the Synthesis of (R)- and (S)-α-Azido Carboxylic Acids," Journal of the American Chemical Society 112(10):4011-4030, May 1990.

Faller, M., et al., "The Structure of a Mycobacterial Outer-Membrane Channel," Science 303(5661):1189-1192, Feb. 2004.

"Focus on Next Generation Sequencing," Nature Biotechnology 26(10):1051-1198, Oct. 2008. [entire issue].

Garaj, S., et al., "Graphene as a Subnanometre Trans-Electrode Membrane," Nature 467(7312):190-193, Sep. 2010.

Gibbs, A.J., and G.A. McIntyre, "The Diagram, a Method for Comparing Sequences: Its Use With Amino Acid and Nucleotide Sequences," European Journal of Biochemistry 16(1):1-11, Sep. 1970.

Girirajan, S., et al., "Phenotypic Heterogeneity of Genomic Disorders and Rare Copy-Number Variants," New England Journal of Medicine 367(14):1321-1331, Oct. 2012.

Gyarfas, B., et al., "Mapping the Position of DNA Polymerase-Bound DNA Templates in a Nanopore at 5 Å Resolution,"ACS Nano 3(6):1457-1466, Jun. 2009.

Heinz, C., et al., "High-Level Expression of the Mycobacterial Porin MspA in *Escherichia coli* and Purification of the Recombinant Protein," Journal of Chromatography B 790(1-2):337-348, Jun. 2003.

Heyn, H., and M. Esteller, "DNA Methylation Profiling in the Clinic: Applications and Challenges," Nature Reviews: Genetics 13(10):679-692, Oct. 2012.

Hogeweg, P., and B. Hesper, "The Alignment of Sets of Sequences and the Construction of Phyletic Trees: An Integrated Method," Journal of Molecular Evolution 20(2):175-186, Jun. 1984.

Hurt, N., et al., "Specific Nucleotide Binding and Rebinding to Individual DNA Polymerase Complexes Captured on a Nanopore," Journal of the American Chemical Society 131(10):3772-3778, Mar. 2009.

Ibarra, B., et al., "Proofreading Dynamics of a Processive DNA Polymerase," EMBO Journal 28(18):2794-2802, Sep. 2009.

Johnson, D.S., et al., "Single-Molecule Studies Reveal Dynamics of DNA Unwinding by the Ring-Shaped T7 Helicase," Cell 129(7):1299-1309, Jun. 2007.

Kasianowicz, J.J., et al., "Characterization of Individual Polynucleotide Molecules Using a Membrane Channel," Proceedings of the National Academy of Sciences USA (PNAS) 93(24):13770-13773, Nov. 1996.

Kim, D.-E., et al., "T7 DNA Helicase: A Molecular Motor That Processively and Unidirectionally Translocates Along Single-Stranded DNA," Journal of Molecular Biology 321(5):807-819, Aug. 2002.

Koren, S., et al., "Hybrid Error Correction and De Novo Assembly of Single-Molecule Sequencing Reads," Nature Biotechnology 30(7):693-700, Jul. 2012.

Kowalczyk, S.W., et al., "Slowing Down DNA Translocation Through a Nanopore in Lithium Chloride," Nano Letters 12(2):1038-1044, Feb. 2012.

Langford, K.W., et al., "Unsupported Planar Lipid Membranes Formed From Mycolic Acids of *Mycobacterium tuberculosis*," Journal of Lipid Research 52(2):272-277, Feb. 2011.

Laszlo, A.H., et al., "Methylation and Hydroxymethylation of CpGs Detected With the Nanopore MspA," Proceedings of the National Academy of Sciences USA (PNAS) 110(47):18904-18909, Nov. 2013.

Lathrop, D.K., et al., "Monitoring the Escape of DNA From a Nanopore Using an Alternating Current Signal," Journal of the American Chemical Society 132(6):1878-1885, Feb. 2010. (Author manuscript PMCID: PMC2913974, available in PMC Feb. 17, 2011, 20 pages.).

Li, J., et al., "Ion-Beam Sculpting at Nanometre Length Scales," Nature 412(6843):166-169, Jul. 2001.

(56) References Cited

OTHER PUBLICATIONS

Lieberman, K.R., et al., "Processive Replication of Single DNA Molecules in a Nanopore Catalyzed by phi29 DNA Polymerase," Journal of the American Chemical Society 132(50):17961-17972, Dec. 2010.
Lobo, I., "Copy Number Variation and Genetic Disease," Nature Education 1(1):65, 2008, 3 pages.
Lu, B., et al., "Origins and Consequences of Velocity Fluctuations During DNA Passage Through a Nanopore," Biophysical Journal 101(1):70-79, Jul. 2011.
Mahfoud, M., et al., "Topology of the Porin MspA in the Outer Membrane of *Mycobacterium smegmatis*," Journal of Biological Chemistry 281(9):5908-5915, Mar. 2006.
Manrao, E.A., et al., "Determining the Resolution of Biological Porin MspA for Nanopore Sequencing," Biophysical Journal 100(3):167a-168a, Suppl. 1, Feb. 2011.
Manrao, E.A., et al., "Nucleotide Discrimination With DNA Immobilized in the MspA Nanopore," PLoS One 6(10):e25723, Oct. 2011, pp. 1-7.
Manrao, E.A., et al., "Reading DNA at Single-Nucleotide Resolution With a Mutant MspA Nanopore and phi29 DNA Polymerase," Nature Biotechnology 30(4):349-353, Mar. 2012. (Author manuscript PMCID: PMC3757088, available in PMC Aug. 29, 2013, 12 pages.).
Matson, S.W., and K.A. Kaiser-Rogers, "DNA Helicases," Annual Review of Biochemistry 59:289-329, Jun. 1990.
Meller, A., et al., "Rapid Nanopore Discrimination Between Single Polynucleotide Molecules," Proceedings of the National Academy of Sciences USA (PNAS) 97(3):1079-1084, Feb. 2000.
Merchant, C.A., et al., "DNA Translocation Through Graphene Nanopores," Nano Letters 10(8):2915-2921, Aug. 2010.
Morin, J.A., et al., "Active DNA Unwinding Dynamics During Processive DNA Replication," Proceedings of the National Academy of Sciences USA (PNAS) 109(21):8115-8120, May 2012.
Nakai, H., and C.C. Richardson, "Interactions of the DNA Polymerase and Gene 4 Protein of Bacteriophage T7. Protein-Protein and Protein-DNA Interactions Involved in RNA-Primed DNA Synthesis," Journal of Biological Chemistry 261(32):15208-15216, Nov. 1986.
Niederweis, M., et al., "Closing of the mspA Gene Encoding a Porin From *Mycobacterium smegmatis*," Molecular Microbiology 33(5):933-945, Sep. 1999.
International Search Report and Written Opinion dated Aug. 15, 2013, issued in corresponding International Application No. PCT/US2013/037454, filed Apr. 19, 2013, 5 pages.
"NIH Funding Opportunity Announcement for RFA-HG-10-012: Revolutionary Genome Sequencing Technologies—The $1000 Genome (R01)," National Institutes of Health, release date Aug. 27, 2010, <http://grants.nih.gov/grants/guide/rfa-files/RFA-HG-10-012.html> [retrieved Nov. 4, 2014], 26 pages.
Pandey, A.K., et al., "Nitrile-Inducible Gene Expression in Mycobacteria," Tuberculosis 89(1):12-16, Jan. 2009.
Papavinasasundaram, K.G., et al., "Construction and Complementation of a recA Deletion Mutant of *Mycobacterium smegmatis* Reveals That the Intein in *Mycobacterium tuberculosis* recA Does Not Affect RecA Function," Molecular Microbiology 30(3):525-534, Nov. 1998.
Pavlenok, M., et al., "MspA Nanopores From Subunit Dimers," PLoS One 7(6):e38726, Jun. 2012, 12 pages.
Pavlov, A.R., et al., "Helix-Hairpin-Helix Motifs Confer Salt Resistance and Processivity on Chimeric DNA Polymerases," Proceedings of the National Academy of Sciences USA (PNAS) 99(21):13510-13515, Oct. 2002.
Pu, Y., et al., "Synthesis and Acylation of Salts of L-Threonine β-Lactone: A Route to β-Lactone Antibiotics," Journal of Organic Chemistry 56(3):1280-1283, Feb. 1991.
Purnell, R.F., and J.J. Schmidt, "Discrimination of Single Base Substitutions in a DNA Strand Immobilized in a Biological Nanopore," ACS Nano 3(9):2533-2538, Sep. 2009.
Purnell, R.F., et al., "Nucleotide Identification and Orientation Discrimination of DNA Homopolymers Immobilized in a Protein Nanopore," Nano Letters 8(9):3029-3034, Sep. 2008.
Rosenstein, J.K., et al., "Integrated Nanopore Sensing Platform With Sub-Microsecond Temporal Resolution," Nature Methods 9(5): 487-492, Mar. 2002.
Salas, M., et al., "The Bacteriophage φ29 DNA Polymerase," IUBMB Life 60(1):82-85, Jan. 2008.
Savage, D.F., et al., Cell-Free Complements In Vivo Expression of the *E. coli* Membrane Proteome, Protein Science 16(5):966-976, May 2007.
Schloss, J.A., "How to Get Genomes at One Ten-Thousandth the Cost," Nature Biotechnology 26(10):1113-1115, Oct. 2008.
Schneider, G.F., et al., "DNA Translocation Through Graphene Nanopores," Nano Letters 10(8):3163-3167, Aug. 2010.
Shimizu, Y., et al., "Cell-Free Translation Systems for Protein Engineering," FEBS Journal 273(18):4133-4140, Sep. 2006.
Shimoboji, T., et al., "Photoresponsive Polymer-Enzyme Switches," Proceedings of the National Academy of Sciences USA (PNAS) 99(26):16592-16596, Dec. 2002.
Smith, S.B., et al., "Overstretching B-DNA: The Elastic Response of Individual Double-Stranded and Single-Stranded DNA Molecules," Science 271(5250):795-799, Feb. 1996.
Soengas, M.S., et al., "Helix-Destabilizing Activity of φ29 Single-Stranded DNA Binding Protein: Effect on the Elongation Rate During Strand Displacement DNA Replication," Journal of Molecular Biology 253(4):517-529, Nov. 1995.
Spirin, A.S., "High-Throughput Cell-Free Systems for Synthesis of Functionally Active Proteins," Trends in Biotechnology 22(10):538-545, Oct. 2004.
Stoddart, D., et al., "Multiple Base-Recognition Sites in a Biological Nanopore: Two Heads Are Better Than One," Angewandte Chemie International Edition 49(3):556-559, Jan. 2010.
Stoddart, D., et al., "Nucleobase Recognition in ssDNA at the Central Constriction of the α-Hemolysin Pore," Nano Letters 10(9):3633-3637, Sep. 2010.
Stoddart, D., et al., Single-Nucleotide Discrimination in Immobilized DNA Oligonucleotides With a Biological Nanopore. Proceedings of the National Academy of Sciences USA (PNAS) 106(19):7702-7707, May 2009.
Thömmes, P., et al., "Four Different DNA Helicases From Calf Thymus," Journal of Biological Chemistry 267(9):6063-6073, Mar. 1992.
Timp, W., et al., "DNA Base-Calling From a Nanopore Using a Viterbi Algorithm," Biophysical Journal 102(10):L37-L39, May 2012.
Van Aardenne-Ehrenfest, T., and N.G. De Bruijn, "Circuits and Trees in Oriented Linear Graphs," Simon Stevin 28:203-217, 1951.
Wallace, E.V.B., et al., "Identification of Epigenetic DNA Modifications With a Protein Nanopore," Chemical Communications 46(43):8195-8197, Nov. 2010.
Wanunu, M., et al., "Discrimination of Methylcytosine From Hydroxymethylcytosine in DNA Molecules," Journal of the American Chemical Society 133(3):486-492, Jan. 2011. (Author manuscript PMCID: PMC3081508, available in PMC Jun. 14, 2012, 14 pages.).
Wanunu, M., et al., "Electrostatic Focusing of Unlabelled DNA Into Nanoscale Pores Using a Salt Gradient," Nature Nanotechnology 5(2):160-165, Feb. 2010. (Author manuscript PMCID: PMC2849735, available in PMC Aug. 1, 2010, 13 pages.).
Williams, G.T., et al., "E1a Transactivation of the Human HSP70 Promotor Is Mediated Through the Basal Transcriptional Complex," Molecular and Cellular Biology 9(6):2574-2587, Jun. 1989.
Williams, R.M., and M.-N. IM, "Asymmetric Synthesis of Monosubstituted and α,α-Disubstituted α-Amino Acids via Diastereoselective Glycine Enolate Alkylations," Journal of the Americal Chemical Society 113(24):9276-9286, Nov. 1991.
Wilson, D.M., III, and D. Barsky, "The Major Human Abasic Endonuclease: Formation, Consequences and Repair of Abasic Lesions in DNA," Mutation Research/DNA Repair 485(4):283-307, May 2001.

(56) References Cited

OTHER PUBLICATIONS

Wilson, N.A., et al., "Electronic Control of DNA Polymerase Binding and Unbinding to Single DNA Molecules," ACS Nano 3(4):995-1003, Apr. 2009.

Winters-Hilt, S., and C. Baribault, "A Novel, Fast, HMM-With-Duration Implementation—for Application With a New, Pattern Recognition Informed, Nanopore Detector," BMC Bioinfomnatics 8(Suppl. 7):S19, Nov. 2007, pp. 1-17.

Yusko, E.C., et al., "Controlling Protein Translocation Through Nanopores With Bio-Inspired Fluid Walls," Nature Nanotechnology 6(4):253-260, Apr. 2011. (Author manuscript PMCID: PMC3071889, available in PMC Oct. 1, 2011, 20 pages.).

Clarke, J., et al., "Continues Base Identification for Single-Molecule Nanopore DNA Sequencing," Nature Nanotechnology 4:265-270, Feb. 22, 2009.

Cherf, G.M., et al., "Automated Forward and Reverse Ratcheting of DNA in a Nanopore at 5-Å Precision," Nature Biotechnology 30(4):344-348, Apr. 2002.

\* cited by examiner

SEQUENCE LISTING

```
<160> NUMBER OF SEQ ID NOS: 18

<210> SEQ ID NO 1
<211> LENGTH: 256
<212> TYPE: DNA
<213> ORGANISM: Artificial Sequence
<220> FEATURE:
<223> OTHER INFORMATION: Synthetic

<400> SEQUENCE: 1 ctttcttcc tctcccaaa agaaataaac aaggaagtaa gcaatgaatt aatcaacgaa        60
ctaaccagag atagacaggg aggtaggcag tgagttagtc agcgagctag ccatatacat      120
ggatgtatgc attgatttat tcatcgatct atccacacgg acgtacgcac tgacttactc      180
accgacctac ccggggtggg cggttggtcg gctggccgtg tgcgtttgtt cgtctgtccg      240
cgcttgctcg cctgcc                                                      256

<210> SEQ ID NO 2
<211> LENGTH: 32
<212> TYPE: DNA
<213> ORGANISM: Artificial Sequence
<220> FEATURE:
<223> OTHER INFORMATION: Synthetic
```

<400> SEQUENCE: 2
cttttcttcc tctccccaaa agaaataaac aa                    32

<210> SEQ ID NO 3
<211> LENGTH: 32
<212> TYPE: DNA
<213> ORGANISM: Artificial Sequence
<220> FEATURE:
<223> OTHER INFORMATION: Synthetic

<400> SEQUENCE: 3
ggaagtaagc aatgaattaa tcaacgaact aa                    32

<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
ccagagatag acagggaggt aggcagtgag tt                    32

<210> SEQ ID NO 5
<211> LENGTH: 32
<212> TYPE: DNA
<213> ORGANISM: Artificial Sequence
<220> FEATURE:
<223> OTHER INFORMATION: Synthetic

<400> SEQUENCE: 5
agtcagcgag ctagccatat acatggatgt at                    32

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
gcattgattt attcatcgat ctatccacac gg                    32

<210> SEQ ID NO 7
<211> LENGTH: 32
<212> TYPE: DNA
<213> ORGANISM: Artificial Sequence
<220> FEATURE:
<223> OTHER INFORMATION: Synthetic

<400> SEQUENCE: 7
acgtacgcac tgacttactc accgacctac cc                    32

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
ggggtgggcg gttggtcggc tggccgtgtg cg                    32

<210> SEQ ID NO 9

```
<211> LENGTH: 32
<212> TYPE: DNA
<213> ORGANISM: Artificial Sequence
<220> FEATURE:
<223> OTHER INFORMATION: Synthetic

<400> SEQUENCE: 9
tttgttcgtc tgtccgcgct tgctcgcctg cc                                    32

<210> SEQ ID NO 10
<211> LENGTH: 14
<212> TYPE: DNA
<213> ORGANISM: Artificial Sequence
<220> FEATURE:
<223> OTHER INFORMATION: Synthetic

<400> SEQUENCE: 10
ccttccaaaa aaaa                                                        14

<210> SEQ ID NO 11
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: Wherein the N at position 38 is an abasic site

<400> SEQUENCE: 11
cttttcttcc tctccccaaa agaaataaac aaggaagncc ttccaaaaaa aa              52

<210> SEQ ID NO 12
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: Wherein the N at position 38 is an abasic  site

<400> SEQUENCE: 12
ggaagtaagc aatgaattaa tcaacgaact aaccagancc ttccaaaaaa aa              52

<210> SEQ ID NO 13
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: Wherein the N at position 38 is an abasic site

<400> SEQUENCE: 13
ccagagatag acagggaggt aggcagtgag ttagtcancc ttccaaaaaa aa              52

<210> SEQ ID NO 14
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (38)..(38)
<223> OTHER INFORMATION: Wherein the N at position 38 is an abasic site

<400> SEQUENCE: 14
agtcagcgag ctagccatat acatggatgt atgcattncc ttccaaaaaa aa          52

<210> SEQ ID NO 15
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: Wherein the N at position 38 is an abasic site

<400> SEQUENCE: 15
gcattgattt attcatcgat ctatccacac ggacgtancc ttccaaaaaa aa          52

<210> SEQ ID NO 16
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: Wherein the N at position 38 is an abasic site

<400> SEQUENCE: 16
acgtacgcac tgacttactc accgacctac ccggggtncc ttccaaaaaa aa          52

<210> SEQ ID NO 17
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: Wherein the N at position 38 is an abasic site

<400> SEQUENCE: 17
ggggtgggcg gttggtcggc tggccgtgtg cgtttgtncc ttccaaaaaa aa          52

<210> SEQ ID NO 18
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: Wherein the N at position 38 is an abasic site

<400> SEQUENCE: 18
tttgttcgtc tgtccgcgct tgctcgcctg ccctttcncc ttccaaaaaa aa          52
```

METHODS AND COMPOSITIONS FOR GENERATING REFERENCE MAPS FOR NANOPORE-BASED POLYMER ANALYSIS

CROSS-REFERENCE TO RELATED APPLICATION

This application is a continuation of U.S. application Ser. No. 14/395,793, filed Oct. 20, 2014, which is a National Stage application of International Application No. PCT/US2013/037454, filed Apr. 19, 2013, which claims the benefit of U.S. Provisional Application No. 61/635,768, filed Apr. 19, 2012, each of which is incorporated herein by reference in its entirety.

STATEMENT OF GOVERNMENT LICENSE RIGHTS

This invention was made with Government support under NHGRI R01HG005115 and HG006321 awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 71232_Seq_Final_2020-03-02.txt. The text file is 5 KB; was created on Apr. 19, 2013; and is being submitted via EFS-Web with the filing of the specification.

BACKGROUND

The rapid, reliable, and cost-effective analysis of polymer molecules, such as sequencing of nucleic acids and polypeptides, is a major goal of researchers and medical practitioners. The ability to determine the sequence of polymers, such as a nucleic acid sequence in DNA or RNA, has additional importance in identifying genetic mutations and polymorphisms. Established DNA sequencing technologies have considerably improved in the past decade but still require substantial amounts of DNA and several lengthy steps and struggle to yield contiguous readlengths of greater than 100 nucleotides. This information must then be assembled "shotgun" style, an effort that depends non-linearly on the size of the genome and on the length of the fragments from which the full genome is constructed. These steps are expensive and time-consuming, especially when sequencing mammalian genomes.

Nanopore-based analysis methods have been investigated as an alternative to traditional polymer analysis approaches. These methods involve passing a polymeric molecule, for example single-stranded DNA ("ssDNA"), through a nanoscopic opening while monitoring a signal such as an electrical signal that is influenced by the physical properties of the target molecule as it passes through the nanopore opening. The nanopore optimally has a size or three-dimensional configuration that allows the polymer to pass only in a sequential, single file order. Under theoretically optimal conditions, the polymer molecule passes through the nanopore at a rate such that the passage of each discrete monomeric subunit of the polymer can be correlated with the monitored signal. Differences in the chemical and physical properties of the monomeric subunits that make up the polymer, for example, the nucleotides that compose the ssDNA, result in characteristic electrical signals. However, nanopores that have been heretofore used for analysis of DNA and RNA, for example, protein nanopores held within lipid bilayer membranes and solid state nanopores, have generally not been capable of reading a sequence at a single-nucleotide resolution. Accordingly, the monitored signals must undergo a deconvolution step to deduce a correlation between the observed signal and the physical characteristics of the monomeric subunits passing through the nanopore. Furthermore, minor fluctuations in assay conditions or nanopore characteristics can differentially influence the monitored signals produced, thus making comparisons between assays, even ones using the same pore, difficult.

Accordingly, a need remains to efficiently correlate the observed signals from existing and future nanopore-based analysis systems to reliably ascertain the physical characteristics of the polymers applied thereto. The methods of the present disclosure addresses this and related needs of the art.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides a method for generating reference signals for polymer analysis in a nanopore system wherein the nanopore system has a multi-subunit output signal resolution. The method comprises translocating a reference sequence through a nanopore of the nanopore system to generate a plurality of reference output signals, wherein each possible multi-subunit sequence that can determine an output signal appears only once in the reference sequence. The method also comprises compiling the plurality of reference output signals into a reference map for nanopore analysis of an analyte polymer.

In some embodiments, the output signal is an ion current through the nanopore. In some embodiments, the ion current is determined by the identities of a plurality of contiguous polymer subunits disposed in a constriction region of the nanopore. In some embodiments, the plurality of contiguous polymer subunits that determine the ion current output signal comprise a dimer, trimer, quadromer, pentamer, hexamer, heptamer, octamer, nonamer or decamer of polymer subunits.

In some embodiments, the reference sequence is a De Bruijn sequence B represented by B(k, n), wherein k is the number of potential polymer subunit identities, and wherein n is the number of contiguous polymer subunits that correspond to the resolution of the nanopore system. In some embodiments, the De Bruijn sequence is generated by taking a Hamiltonian path of an n-dimensional graph over k subunit identities, taking a Eulerian cycle of a (n−1)-dimensional graph over k subunit identities, using finite fields analysis, or concatenating all possible Lyndon words whose length divides by n.

In some embodiments, a segment of the reference sequence or the entire reference sequence is a reference sequence domain of a reference polymer. In some embodiments, the reference sequence domain of the reference polymer consists of the entire reference sequence. In some embodiments, the reference sequence domains of a plurality of distinct reference polymers each consists of an exclusive segment of the reference sequence, wherein the aggregate of the plurality of reference sequence domains contains the entire reference sequence. In some embodiments, each of the plurality of reference polymers further comprises an overlap domain proximal to the reference sequence domain, wherein the overlap domain consists of a 1-50 subunit polymer sequence appearing in the reference domain of another reference polymer.

In some embodiments, the reference polymer further comprises a marker domain with a noncanonical polymer subunit. In some embodiments, the noncanonical polymer subunit is a nucleic acid subunit selected from the group consisting of uracil, 5' methylcytosine, 5' hydroxymethyl-cytosine, 5' formethylcytosine, 5' carboxycytosine b-gluco-syl-5-hydroxy-methylcytosine, 8-oxoguanine, or an abasic lesion.

In some embodiments, the reference polymer further comprises a calibration domain with a polymer sequence predetermined to provide a pattern of multiple output signals. In some embodiments, the analyte polymer comprises the same calibration domain as the reference polymer.

In some embodiments, the analyte polymer is a nucleic acid and the reference sequence is a nucleic acid sequence. In some embodiments, the nucleic acid is single stranded DNA or double stranded DNA. In some embodiments, the DNA nucleic acid comprises or consists of the canonical adenine, thymine, guanine and/or cytosine subunits. In some embodiments, the nucleic acid is RNA. In some embodiments, the RNA nucleic acid comprises or consists of the canonical adenine, uracil, guanine and/or cytosine subunits.

The method of claim 1, wherein the analyte polymer is a polypeptide and the reference sequence is a polypeptide sequence.

The method of claim 1, further comprising comparing one or more output signals generated by the nanopore system using an analyte polymer against the reference library to determine a characteristic of the target polymer.

In some embodiments, the characteristic of the analyte polymer is a sequence pattern of the target polymer. In some embodiments, the characteristic of the analyte polymer is a primary sequence of the target polymer. In some embodiments, the reference sequence is translocated through the nanopore by an electrophoretic and/or an enzymatic mechanism. In some embodiments, the analyte polymer is translocated through a nanopore by the same mechanism as the reference sequence.

In another aspect, the disclosure provides a method for assessing the utility of a nanopore system for polymer analysis, wherein the nanopore system has a multi-subunit output signal resolution. The method comprises translocating a reference sequence through a nanopore of the nanopore system to generate a plurality of reference output signals, wherein each possible multi-subunit sequence that can determine an output signal appears only once in the reference sequence. The method also comprises compiling the plurality of reference output signals into a reference map. The method also comprises determining the frequency of degenerate output signals, whereby a low level of degeneracy is indicative of a high utility of the nanopore system for polymer analysis.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A illustrates a cross-sectional view of a representative nanopore 10 and related system components for polymer analysis. The illustrated system incorporates a protein nanopore 10 embedded in a lipid bilayer 20. A DNA polymerase 40 is bound to the DNA analyte, which contains a single stranded DNA (ssDNA) segment 30 and a double stranded DNA (dsDNA) segment 50. As illustrated, the ssDNA polymer 30 is translocating from the cis side 80 to the trans side 90 of the nanopore 10, as indicated by the directional arrows. As the ssDNA 30 translocates, a blocking oligomer 60 is unzipped (i.e., decomplemented) away from the ssDNA analyte 30 template by pull force exerted on the DNA analyte. Once the blocking oligomer 60 is completely unzipped from the ssDNA template, an extendible end of the double stranded DNA segment 50 is exposed and capable of extension by the DNA polymerase 40 (see FIG. 1B below).

FIG. 1B illustrates a cross-sectional view of the representative nanopore 10 and related system components illustrated in FIG. 1A. However, in this illustration, the ssDNA polymer 30 is translocating from the trans side 90 to the cis side 80 of the nanopore 10, as indicated by the directional arrows. In this stage, the polymerase activity of the DNA polymerase 40 pulls the ssDNA 30 through the nanopore 10 as it incorporates dNTPs 70 to extend the double stranded portion 50 of the analyte using the ssDNA 10 as the template.

DETAILED DESCRIPTION

The present disclosure generally relates to the methods to efficiently analyze polymer characteristics using nanopore-based assays.

Nanopores hold promise for inexpensive, fast, and nearly "reagent-free" analysis of polymers. In a general embodiment, an external voltage is applied across a nanometer-scale, electrolyte filled pore inducing an electric field. Any analyte, such as a polymer, that resides in, or moves through, the interior of the pore modulates the ionic current that passes through the pore depending on its physical characteristics. If the interior tunnel formed by the pore is of sufficiently small diameter and length, polymers that pass through must pass in a linear fashion, such that only a subset of the polymer subunits reside in the most constricted zone of the pore tunnel at one time. Thus, the ionic current fluctuates over time as the polymer passes through the nanopore, subunit by subunit, depending on the different physical characteristics of the subunit(s) residing in the nanopore constriction zone at each iterative step.

Ideally, a polymer in a nanopore will generate a unique output signal, such as a current level, that is determined by a single, monomeric subunit of the polymer residing in the pore at each iterative translocation step. Thus, as the polymer translocates the resulting trace of output signals can be translated directly into the primary sequence of the polymer. However, most nanopores have constriction zones that physically interact with more than one polymer subunit during any single translocation event and thus the magnitude of the ion current is influenced by more than one subunit. Accordingly, the resulting output signal reflects a plurality of subunits. Each output signal then must be correlated to signals produced by known combinations of polymer subunits. Thus, for polymer analysis, a reference map is required to deduce the sequence or other physical characteristics of the analyte polymer.

The present inventors have developed an efficient approach to generating a reference map for any nanopore system capable of translocating a polymer. The approach, described herein, has the advantages of minimizing the length of the reference sequence required to generate a comprehensive reference map for any polymer where the subunits are known. This results in reduced costs and efforts in generating reference polymers, reduced translocation complications associated with overlong reference polymers, and wide applicability to various nanopore-types.

In accordance with the foregoing, in one aspect, the present disclosure provides a method for generating reference signals for polymer analysis in a nanopore system. The nanopore systems addressed by the present disclosure have a multi-subunit output signal resolution. The method comprises translocating a reference sequence through a nanopore of the nanopore system to generate a plurality of reference output signals, wherein every or substantially every possible multi-subunit sequence that can determine an output signal appears only once in the reference sequence; and compiling the plurality of reference output signals into a reference map for nanopore analysis of an analyte polymer. In some embodiments, every possible multi-subunit sequence that can determine an output signal appears in the reference sequence. In some embodiments, every possible multi-subunit sequence that can determine an output signal appears in the reference sequence only once. In some embodiments, substantially every possible multi-subunit sequence that can determine an output signal appears in the reference sequence. In some embodiments, substantially every possible multi-subunit sequence that can determine an output signal appears in the reference sequence only once.

Many aspects of the nanopore systems of the present disclosure are familiar in the art. Typically, a pore is disposed within a nonconductive barrier between a first conductive liquid medium and a second conductive liquid medium. The nanopore, thus, provides liquid communication between the first and second conductive liquid media. In some embodiments, the pore provides the only liquid communication between the first and second conductive liquid media. The liquid media typically comprises electrolytes or ions that can flow from the first conductive liquid medium to the second conductive liquid medium through interior of the nanopore. Additionally, the analyte polymer as the target or focus of an analysis is capable of entering the nanopore and translocating, preferably in a linear fashion, through the pore to the other side. In some cases, the first and second conductive liquid media located on either side of the nanopore are referred to as being on the cis and trans regions, where the analyte polymer to be measured generally translocates from the cis region to the trans region through the nanopore. However, in some embodiments, the analyte polymer to be measured can translocate from the trans region to the cis region through the nanopore. In some cases, the polymer as a whole does not pass through the pore, but portions or segments of the polymer pass through the nanopore for analysis.

Nanopores useful in the present disclosure include any nanopore capable of permitting the linear translocation of a polymer from one side to the other at a velocity amenable to monitoring techniques, such as techniques to detect current fluctuations. In some embodiments, the nanopore comprises a protein, such as alpha-hemolysin or MspA. Protein nanopores have the advantage that, as biomolecules, they self-assemble and are essentially identical to one another. In addition, it is possible to genetically engineer protein nanopores to confer desired attributes, such as substituting amino acid residues for amino acids with different charges, or to create a fusion protein (e.g., an exonuclease+alpha-hemolysin). Thus, the protein nanopores can be wild-type or can be modified. For example, for descriptions of modifications to MspA nanopores, see U.S. Pat. Pub. No. 2012/0055792. In some cases, the nanopore is disposed within a membrane, or lipid bilayer, which can separate the first and second conductive liquid media. In some embodiments, the nanopore can be a solid state nanopore. Solid state nanopores can be produced as described in U.S. Pat. Nos. 7,258,838 and 7,504,058. Solid state nanopores have the advantage that they are more robust and stable. Furthermore, solid state nanopores can in some cases be multiplexed and batch fabricated in an efficient and cost-effective manner Finally, they might be combined with micro-electronic fabrication technology. In some cases, the nanopore comprises a hybrid protein/solid state nanopore in which a nanopore protein is incorporated into a solid state nanopore.

Figure 1A:
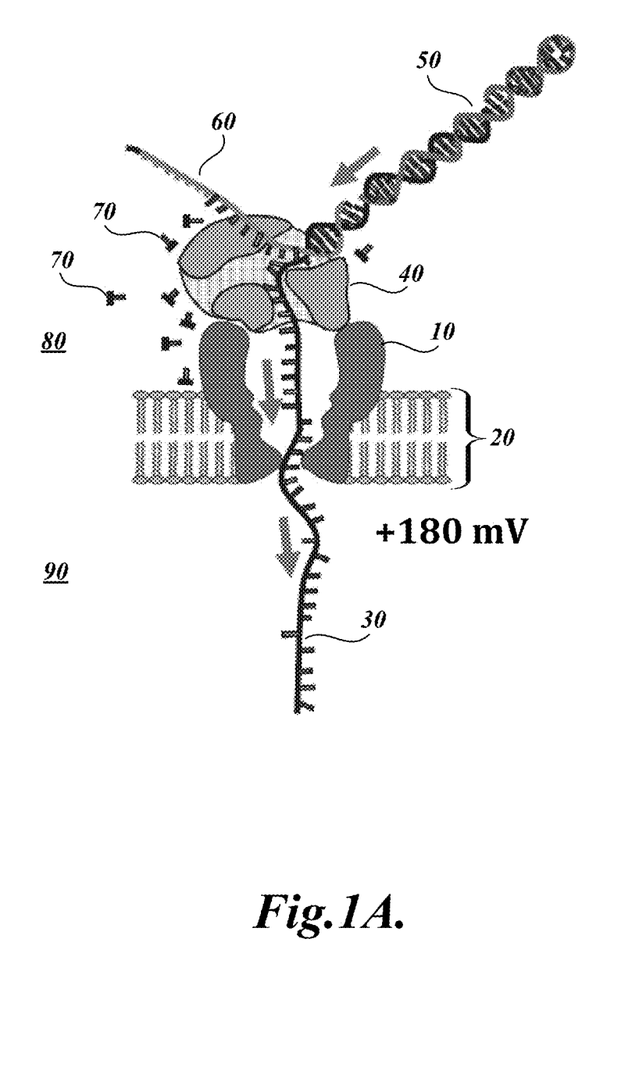
Figure 1B:
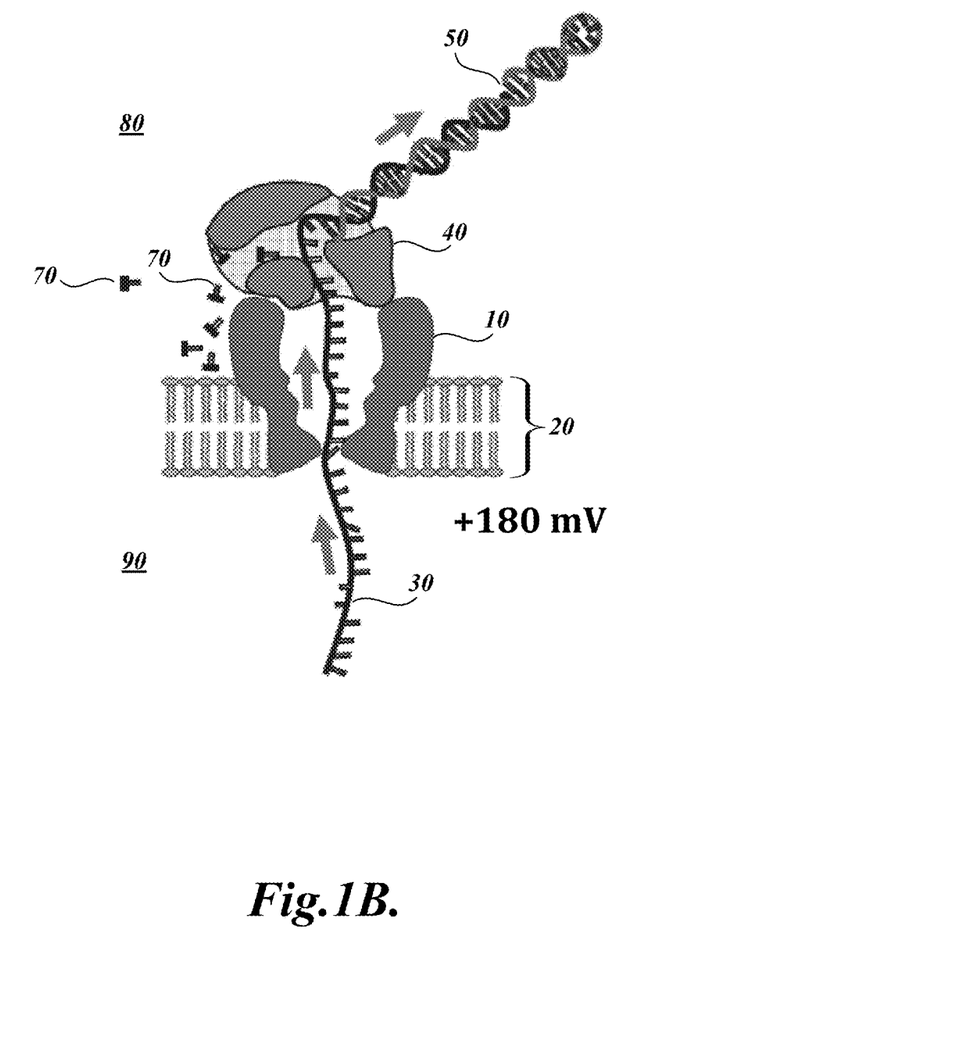

The analyte polymer and/or reference sequence can be translocated through the nanopore using a variety of mechanisms. For example, the analyte polymer and/or reference sequence can be electrophoretically translocated through the nanopore. Additionally or alternatively, nanopore systems can include a component that translocates a polymer through the nanopore enzymatically. For example, a molecular motor can be included to influence the translocation of polymers through the nanopore. A molecular motor can be useful for facilitating entry of a polymer into the nanopore and/or facilitating or modulating translocation of the polymer through the nanopore. Ideally, the translocation velocity, or an average translocation velocity is less than the translocation velocity that would occur without the molecular motor. In any embodiment herein, the molecular motor can be an enzyme, such as a polymerase, an exonuclease, or a Klenow fragment. In one example, described in more detail below and illustrated in FIGS. 1A-1B, a DNA polymerase such as phi29 can be used to facilitate movement in both directions. See also Cherf, G. M., et al., "Automated forward and reverse ratcheting of DNA in a nanopore at 5-Å precision," *Nat. Biotechnol.* 30:344-348 (2012). It is preferred that the output signals generated from an analyte polymer were generated in a system where the analyte polymer was translocated using the same mechanism that was used to translocate the reference sequence through its nanopore, which can be the same or different nanopore.

Nanopore systems also incorporate structural elements to apply a voltage across the nanopore-bearing membrane or film. For example, the system can include a pair of drive electrodes that drive current through the nanopores. Additionally, the system can include one or more measurement electrodes that measure the current through the nanopore. These can be a patch-clamp amplifier or a data acquisition device. For example, nanopore systems can include an Axopatch-1B patch-clamp amplifier (Axon Instruments) to apply voltage across the bilayer and measure the ionic current flowing through the nanopore.

The disclosed methods are useful for nanopore systems that have a multi-subunit output signal resolution. As used herein, the term "multi-subunit output signal resolution" refers to the characteristic of the nanopore where any output signal, e.g., a measurable current level through the pore, is determined or influenced by the physical characteristics of two or more polymer subunits residing therein. Typically, the polymer subunits that determine or influence the output signal reside at that time in the "constriction zone," or three-dimensional region in the interior of the pore with the narrowest diameter. Depending on the length of the constriction zone, the number of polymer subunits that influence the passage of electrolytes, and thus current output signal, can vary. The output signal produced by the nanopore system is any measurable signal that provides a multitude of distinct and reproducible signals depending on the physical characteristics of the polymer or polymer subunits. For example, the current level through the pore is an output signal that can vary depending on the particular polymer subunit(s) residing in the constriction zone of the nanopore. As the polymer passes in iterative steps (e.g., subunit by subunit), the current levels can vary to create a trace of multiple output signals.

As used herein, the term "polymer" refers to a chemical compound comprising two or more repeating structural units, referred to herein interchangeably as "subunits," "monomeric units," or "mess," where each subunit can be the same or different. Nonlimiting examples of polymers to be analyzed with the present methods include: nucleic acids, peptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). Polymers include copolymers, block copolymers, and branched polymers such as star polymers and dendrimers. The term "nucleic acid" refers to a deoxyribonucleotide polymer (DNA) or ribonucleotide polymer (RNA) in either single- or double-stranded form. The structure of the canonical polymer subunits of DNA, for example, are commonly known and are referred to herein as adenine (A), guanine (G), cytosine (C), and thymine (T). As a group, these are generally referred to herein as nucleotides or nucleotide residues. For RNA, the 20 canonical polymer subunits are the same, except with uracil (U) instead of thymine (T). Similarly, the structures of the canonical polymer subunits of polypeptides are known, and are referred to as a group herein as amino acids or amino acid residues.

As described above, the methods of the present disclosure are useful for nanopore systems with multi-subunit signal resolution. Thus, the output signal, such as the ion current through the nanopore, is determined or influenced by more than one polymer subunit in the nanopore constriction site at any given time. In some embodiments, the resolution or output signal is determined by two or more contiguous polymer subunits in the nanopore at any given time. In some embodiments, the two or more contiguous polymer subunits are in the constriction zone of the nanopore thereby influencing the output signal. Embodiments include nanopore systems where the output signal is determined by two, three, four, five, six, seven, eight, nine, 10, 11, 12, 13, 14, 15, 16, 17, 18, 19, 20, or more contiguous polymer subunits residing in the constriction zone of the nanopore at the time the output signal is measured (e.g., at the time the current level is measured). It is noted that the multi-subunit polymer sections that determine the output signal in the nanopore system can be referred to as "-mers", such as 2-mer, 3-mer, 4-mer, 5-mer, 6-mer, 7-mer, 8-mer, 9-mer, 10-mer, etc. Alternatively, the multi-subunit polymer sections can be referred to as a dimer, trimer, quadromer, pentamer, hexamer, heptamer, octamer, nonamer, decamer, etc. As described, the multi-subunit polymer sections influence the output signal, such as current level, because when residing in the narrow constriction zone, the physical properties of each subunit impedes the current flow through the nanopore. Thus, the identities of each subunit has an influence on, and is reflected in, the overall current level at that time.

The disclosed method comprises translocating a reference sequence through a nanopore of the nanopore system to generate a plurality of reference output signals. The reference sequence can be translocated electrophoretically by applying voltage to the system. Alternatively, or simultaneously, the sequence can be pulled or pushed through the nanopore, for example, with the action of a molecular motor.

The reference sequence is optimally one where each possible multi-subunit sequence that can determine an output signal appears only once in the reference sequence. Thus the reference sequence is optimized to be as short as possible while providing every potential multi-subunit sequence that corresponds with the resolution of the nanopore system. For example, a nanopore system that as a resolution of four subunits generates an output signal determined or influenced by a quadromer of the polymer subunits. Thus the reference sequence for this nanopore will have every possible quadromer sequence in as short a sequence as possible. This provides a distinct and surprising advantage of reducing the efforts and costs expended on reference sequence synthesis and the time and effort for applying the reference sequences to the nanopore system.

An optimized reference sequence with each multi-subunit appearing only once can be designed by generating a De Bruijn sequence. A De Bruijn B sequence is represented by $B(k, n)$, wherein k is the number of potential polymer subunit identities, and wherein n is the number of contiguous polymer subunits that correspond to the resolution of the nanopore system. A De Bruijn sequence that is represented as a circular cyclic sequence (i.e., with no beginning or end) will have a length of $k^n$. The De Bruijn sequence can be generated by taking a Hamiltonian path of an n-dimensional graph over k subunit identities, taking a Eulerian cycle of a (n−1)-dimensional graph over k subunit identities, using finite fields analysis, or concatenating all possible Lyndon words whose length divides by n. An exemplary De Bruijn sequence $B(4,4)$ (k is four to reflect the four possible nucleotide residues of the DNA "alphabet"; n is four to reflect a quadromer polymer segment that determines the output signal for some MspA-based nanopores systems) is set forth herein as SEQ ID NO:1 in linear form with an arbitrary start and end point. However, it should be noted that linearization of a cyclic or circular De Bruijn sequence interrupts the contiguity of (n−1) multi-subunit segments, depending on the length of the segments n. For instance, for a De Bruijn reference sequence of quadromers, a linearizing breakpoint in the circular sequence interrupts the contiguity of three of the quadromers. Accordingly, three additional polymer subunits must be added to one end of the linear sequence to meet the criteria of having every possible quadromer appearing once.

Under some conditions, some multi-subunit sequences are difficult to synthesize or otherwise provide in a reference sequence. Accordingly it is understood that in some embodiments, fewer than every possible multi-subunit sequence that can determine an output signal appears only once in the reference sequence. For example, substantially every multi-subunit sequence appears in the reference sequence. In this context, "substantially every possible multi-subunit sequence" refers to at least 90% of every possible multi-subunit sequence that can determine an output signal, such as 90%, 91%, 92%, 93%, 94%, 95%, 96%, 97%, 98%, or 99% of every possible multi-subunit sequence that can determine an output signal appears in the reference sequence.

Additionally, under some conditions, it may be desirable to introduce some sequence redundancy into the reference sequence itself. Such conditions can include difficulties of generating clear output signals due to secondary structure or differential translocation speed associated with particular sub-sequences. However, to maintain the advantages of the present disclosure, such redundancy is minimized. Accordingly, in some embodiments, at least 90%, 91%, 92%, 93%, 94%, 95%, 96%, 97%, 98%, or 99% of every possible multi-subunit sequence appears only once in the reference sequence. Consequently, the present disclosure encompasses embodiments where 10%, 9%, 8, 7, 6, 5, 4, 3, 2, or 1% of every possible multi-subunit sequence can appear more than once in the reference sequence, such as appearing two, three, four, or more times in the reference sequence.

In some embodiments, the entire reference sequence, which may consist of one of each multi-subunit polymer segment that can determine a signal output, is a reference sequence domain of a reference polymer molecule or construct. In some embodiments, the entire reference sequence is a reference sequence domain of a single reference polymer molecule or construct. In alternative embodiments, the reference sequence is segmented into reference subsequences. The reference sub-sequences or segments are mutually exclusive, meaning that there are no multi-subunit polymer sub-sequences in common among the reference sub-sequences or segments. For example, a De Bruijn sequence was developed for DNA to generate a quadromer map (for nanopores with output signals determined by four nucleotides) and segmented into eight subsequences, set forth herein as SEQ ID NOS:2-9. In some further embodiments, the reference sub-sequences or segments can be reference domains in a plurality of distinct reference polymers, as provided in Table 1, below. Each of the plurality of distinct reference polymers contains a distinct reference domain. The aggregate of the reference domains can be aligned or reassembled to provide the entire reference sequence without redundancy or extraneous polymer subunits.

As described above, when a breakpoint is introduced into a De Bruijn sequence, additional n−1 subunits must be added at one end to preserve the contiguity of all multi-subunit segments. Accordingly, in some embodiments, each of the plurality of reference polymers further comprises an overlap domain proximal to the reference sequence domain, wherein the overlap domain consists of a 3-50 subunit polymer sequence appearing in the reference domain of another reference polymer. As used herein, the term "proximal" refers to the position directly preceding or subsequent to the reference position. In terms of DNA sequence, for example, the overlap domain is immediately 5' or 3' to the reference domain without intervening nucleotide residues. This restores the contiguity of the fragmented multi-subunit segments and allows for signal trace overlap (and adjustment) of traces generated from distinct reference polymers. The overlap domain corresponds to a subunit polymer sub-sequence appearing in a different reference domain. In the context of DNA polymers, typically, an overlap domain added to the 3' end of a first reference domain will correspond to (e.g., repeat) the sub-sequence at the 5' end of a second reference domain. Alternatively, an overlap domain added to the 5' end of a first reference domain will correspond to (e.g., repeat) the subsequence at the 3' end of a second reference domain. This type of configuration is illustrated for a group of eight reference domains and corresponding overlap domains in Table 1.

In some embodiments, the one or more reference polymers further comprise a marker domain with a noncanonical polymer subunit. A noncanonical subunit is useful to provide an obvious output signal to indicate that the end of the reference domain (and possibly overlap domain) has passed through the nanopore. Regarding embodiments of nucleic acid polymers, illustrative and nonlimiting examples of noncanonical subunits include uracil (for DNA), 5-methylcytosine, 5-hydroxymethylcytosine, 5-formethylcytosine, 5-carboxycytosine b-glucosyl-5-hydroxy-methylcytosine, 8-oxoguanine, 2-amino-adenosine, 2-amino-deoxyadenosine, 2-thiothymidine, pyrrolo-pyrimidine, 2-thiocytidine, or an abasic lesion. An abasic lesion is a location along the deoxyribose backbone but lacking a base. Representative noncanonical peptide residues are known in the art, as set forth in, for example, Williams et al., *Mol. Cell. Biol.* 9:2574 (1989); Evans et al., *J. Amer. Chem. Soc.* 112:4011-4030 (1990); Pu et al., *J. Amer. Chem. Soc.* 56:1280-1283 (1991); Williams et al., *J. Amer. Chem. Soc.* 113:9276-9286 (1991); and all references cited therein. Exemplary noncanonical amino acids include, but are not limited to: 2-Aminoadipic acid, N-Ethylasparagine, 3-Aminoadipic acid, Hydroxylysin, β-alanine, β-Amino-propionic acid, allo-Hydroxylysine, 2-Aminobutyric acid, 3-Hydroxyproline, 4-Aminobutyric acid, piperidinic acid, 4-Hydroxyproline, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, N-Ethylglycine. Methods of incorporating noncanonical amino acids are well known in the art.

In some embodiments, the reference polymer further comprises a calibration domain. In some embodiments, the calibration domain comprises a polymer sequence predetermined to provide a recognizable pattern of multiple output signals. In some embodiments, the multiple output signals are highly distinct to facilitate the pattern being easily recognizable. Thus, each output signal can be mutually distinguished with a high degree of reliability. For example, a useful pattern can be one that provides a high-low-high or a low-high-low current fluctuation. In some embodiments, both the high and the low current levels of the multiple output signals are near the extreme ends of the spectrum of possible output signal produced by multi-subunit polymer segments. This is useful to calibrate a plurality of signal (e.g., current) traces from different polymers. Because the calibration sequence is the same in each polymer (reference or analyte), the sequence pattern will be the same for every polymer. However, various assay conditions might fluctuate from assay to assay, thus causing the pattern to drift or shift upward or downward or changing conductance causing a variation in the calibration constant. Such changing conditions can include temperature, applied voltage, salinity of the conductive media, nanopore shape, etc. Using a calibration domain in every polymer where the domain contains a common sequence allows for the normalization of all sequence traces to a standardized set of levels. Furthermore, the calibration sequence can also be included in the analyte DNA and allows for rescaling the ion currents (or other conditions) to the same conditions as the reference oligonucleotide constructs. An exemplary calibration sequence for DNA is CCTTCCAAAAAAAA (set forth herein as SEQ ID NO:10), set forth below. Exemplary DNA reference polymers for generating a quadromer reference map, where the De Bruijn sequence was segmented into eight fragments, and where the reference polymers contain reference, overlap, marker and calibration domains, are provided below in Table 1 and are also set forth as SEQ ID NOS:11-18.

Figure 2:
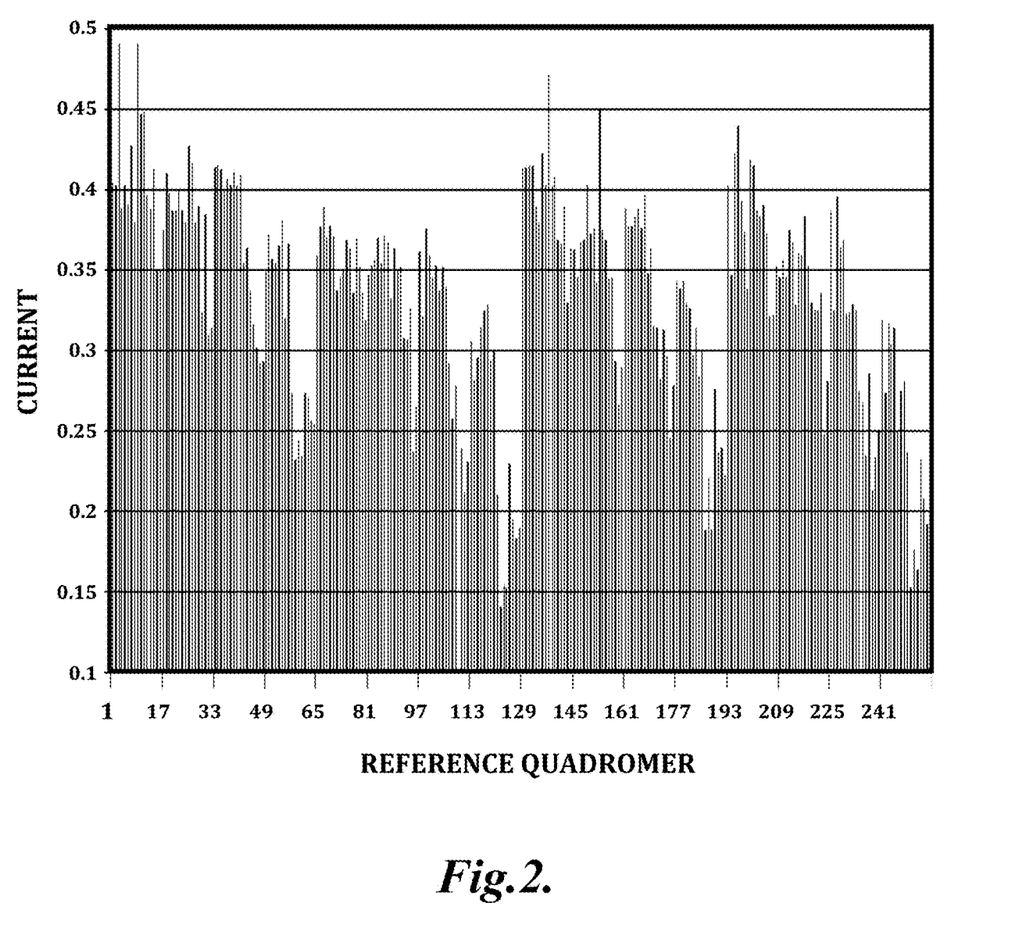
FIG. 2 illustrates a representative quadromer map generated from a reference DNA sequence described herein. The current measurements for all 256 possible nucleotide subunit quadromers are illustrated as a fraction of open pore current. These values require multiplication by ~115 pA to convert to pico ampere units.

In accordance with the disclosed method, a reference sequence (for example, as contained in one or more reference polymers, as described above) appropriate for the resolution of a nanopore system is applied to the nanopore. As described, nanopores generally do not produce output signals that achieve single polymer subunit resolution (i.e., output signals determined exclusively by a single polymer subunit). Nanopores can be readily assayed to determine their level of multi-subunit resolution. For example, test polymers with mostly uniform subunits can be translocated through the nanopore, and the number of output signals affected by the presence of a single, distinct subunit can be determined. An exemplary test polymer is described in Manrao et al., "Nucleotide Discrimination with DNA Immobilized in the MspA Nanopore," *PLoS ONE* 6(10):e25723 (2011). In such a manner, it can be determined for any nanopore/polymer combination how many polymer subunits determine the output signal at each measurement. Once the "word" length (i.e., multi-subunit length) is determined, an optimized reference sequence can then be generated that corresponds to this nanopore resolution that contains every possible multi-subunit word of that length only once. The reference sequence, for example as contained in a single or multiple reference polymers, can be examined with to the nanopore. The output signals are thus generated for every possible multi-subunit segment from the shortest possible reference sequence. The output signals are compiled into a reference map or library that correlates each output signal with the sequence of each possible multi-subunit polymer segment that can generate a discrete output signal. An exemplary quadromer DNA map is described below and illustrated in FIG. 2.

The reference map or library can thereafter be used to determine characteristics of an unknown analyte polymer. Output signals obtained from an analyte polymer are compared to the reference map. It will be understood that the analyte polymer is the same type of polymer as the reference polymer or reference sequence. For example, a reference nucleic acid polymer is used to generate a reference table for use in analyzing an analyte nucleic acid polymer. In some embodiments, the output signals for the analyte polymer are generated in the same type of nanopore as used to generate the output signals used to generate a reference map. As described above, nanopores such as protein nanopores can be generated with a high degree of similarity such that different copies of the same type (e.g., MspA, or one particular mutant thereof) are essentially identical to each other. Thus, a reference library generated using one particular MspA nanopore in a system can be used to analyze the output signals for an analyte measured using another MspA nanopore. As described, slight differences in assay conditions can be normalized using calibration domains present in the different reference and analyte polymers. In some embodiments, the output signals for the analyte polymer are generated in the same nanopore as the output signals from the reference sequence used to generate a reference map.

In some embodiments, the characteristics ascertained from an analyte polymer can be a sequence pattern that does not provide a primary sequence but merely provides a unique and recognizable pattern of subunit structures, such as a "fingerprint." In this regard, the term "fingerprint" is used to refer to sufficient structural or sequence data that can be used to determine whether two polymers are different or whether they are likely the same. Alternatively, the sequence pattern can be the complete or primary sequence or the primary sequence of a portion of the polymer.

In practice, a trace obtained for an analyte polymer can be generated in a nanopore system. Each output signal can be compared to the reference map. When a matching output signal is found, the particular reference multi-subunit sequence is determined to have resided in the nanopore at that specific time of measurement. As a series of sequences are correlated to a series of output signals in the analyte polymer trace, the characteristics of the polymer (e.g., the sequence) can be reconstructed. For some nanopore systems, there will likely be some degeneracy of the output signals, i.e., where two or more distinct multi-subunit polymer sequences result in the same or similar output signal within some margin of error. Thus, when an analyte output signal matches a degenerate reference signal, all possible multi-subunit polymer sequences that correspond to that signal must be considered for that position. An algorithm can be applied to determine which of the multiple possible multi-subunit polymer sequences is correct. For example, Hidden-Markov Models (HMM) are particularly suited for recovering sequence information for this system. See, e.g., Timp W, et al., 2012, *Biophys. J.* 102:L37-L39, incorporated herein by reference. For example, as a general illustration of an embodiment, all potential multi-subunit polymer sequences for a degenerate sequence are stored. A second, subsequent output signal sequence is assessed to provide one or more potential multi-subunit polymer sequences for the second output signal. All potential multi-subunit polymer sequences for the first output signal that are incompatible with the potential multi-subunit polymer sequences for the second output signal are discarded. This process is repeated for more sub-sequence output signals. Thus, even if the first measurement yielded many possible multi-subunit polymer sequences, it is likely that after several measurements there will only be one or a few possible sequences that are consistent with all the measurements.

In another aspect, the disclosure provides compositions useful for performing the methods described above. For example, in some embodiments, the present disclosure provides a reference polymer that comprises a reference domain. In some embodiments, the reference polymer further comprises at least one of a marker domain and a calibration domain. In some embodiments, the present disclosure provides a plurality of reference polymers each comprising a distinct reference domain, wherein the aggregate of the reference domains establish a reference sequence as described above. In some embodiments, the plurality of reference polymers each further comprise an overlap domain as described herein.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Disclosed are materials, compositions, and components that can be used for, can be used in conjunction with, can be used in preparation for, or are products of the disclosed methods and compositions. It is understood that, when combinations, subsets, interactions, groups, etc. of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the material for which they are cited are hereby specifically incorporated by reference in their entireties.

The following is a description of an exemplary approach for generating a current signal in a nanopore-based system reflecting the sequence of target DNA polymers.

In nanopore-based polymer analysis, an ion current is measured as the polymer is passed or drawn through the opening of the nanopore. For DNA, it has been demonstrated that several nucleotides (i.e., an n-mer of DNA monomeric subunits) affect the ion current (see, e.g., Derrington et al., "Nanopore DNA sequencing with MspA," *PNAS* 107(37):16060-16065 (2010); Manrao et al., "Nucleotide Discrimination with DNA Immobilized in the MspA Nanopore," *PLoS ONE* 6(10):e25723 (2011)). In the case of using a preferred nanopore, MspA mutant M2-NNN (MspA with the amino acid substitutions D90N, D91N, D93N, D118R, D134R, and E139K; Butler et al., "Single-molecule DNA detection with an engineered MspA protein nanopore," *PNAS* 105(52):20647-20652 (2008)), it was demonstrated that four nucleotides (i.e., nucleotide quadromers, or 4-mers) are involved in controlling the ion current when the DNA is held from the cis side and 180 mV is applied. When DNA is moved through the pore in single nucleotide steps, a succession of quadromer-generated current values best describes the ion current trace (Manrao et al., *Nature Biotechnology* 30:349-353 (2012)).

Briefly, as described in Manrao et al. (2012), the present inventors combined the previously engineered MspA nanopore (i.e., M2-NNN) with the phi29 DNA Polymerase (DNAP) blocking oligomer technique to read well-resolved and distinguishable current levels as DNA is drawn through the pore. In the assays, a single MspA pore was established in a lipid bilayer separating two chambers (cis and trans) containing 0.3 M KCl buffer solution. A patch-clamp amplifier applied+180 mV to the trans side of the bilayer and measured the ionic current through the pore. Current traces from the MspA-DNA-motor complex were analyzed in the unzipping phase and in the synthesis phase. Schematic illustrations of these phases are provided in FIGS. 1A and 1B, respectively.

For example, to study an easily resolvable DNA sequence, a 'block homopolymer' DNA template was used containing all four bases in short homopolymer sections of adenine (dA3), guanine (dG3) and cytosine (dC5), each separated by thymine (dT3). In control experiments without phi29 DNA polymerase (DNAP), the DNA translocation was too fast (>1 nt/µs) to read individual nucleotides. Next, phi29 DNAP was added to the cis volume, but the divalent cations and deoxyribonucleotide triphosphates (dNTPs) necessary for synthesis were omitted. Translocation events were recorded with current patterns consistent with force-activated unzipping of the blocking oligomer. These events exhibited distinct current levels including a high peak (~0.6 Io) when the two abasic sites passed through the constriction. As expected, after removal of the blocking oligomer, the phi29 DNAP was unable to extend the primer strand owing to the absence of divalent cations and dNTPs. The phi29 DNAP eventually either fell off, allowing cooperative dissociation of the primer in MspA, or continued onwards, unzipping the primer strand. The duration of these events was generally >20 s.

To allow DNA synthesis to proceed, all four standard dNTPs (100 µM each) and 10 mM $MgCl_2$ were added. In five separate experiments using the block homopolymer DNA, 33 events with the same distinct current pattern were observed. A typical current trace was characterized by a rapid succession of current steps (levels) with various durations and current values ranging between 0.18 and 0.4 of $I_o$ and two peaks with current levels above 0.6 $I_o$. Many levels at the beginning of an event were repeated later in the event, but in the opposite order. These results are consistent with part of each DNA molecule being read twice; once, during stepwise motion of the DNA template toward the trans side, while unzipping the blocking oligomer, and again, during stepwise motion back toward the cis side, while phi29 DNAP was synthesizing (see FIGS. 1A and 1B, respectively for an illustration of these phases). The levels observed during unzipping were symmetrical in time with levels observed during synthesis. Once phi29 DNAP completed synthesis of the DNA template strand, both the DNA and phi29 DNAP exited to the cis side. The average duration of events containing phi29 DNAP synthesis (~14 s) was shorter than events recorded in the absence of $Mg^{2+}$ and dNTPs because synthesis is faster than the time for phi29 DNAP to release from the DNA template or to unzip the primer strand. In the experiments with $MgCl_2$ and dNTPs, >10% of the total data acquisition time was spent with a DNA-motor complex threaded through MspA.

The temporal ordering of the current levels was preserved across all traces and that the levels could be aligned with the known DNA sequence. The results were qualitatively consistent with the inventors' previous work (Manrao et al. (2011)) where homopolymer DNA was held statically in MspA by a NeutrAvidin molecule. The sequence of the DNA to the current levels were qualitatively aligned by assuming equal spacing of nucleotides and matching the position of the current peak associated with the abasic lesion, the turnaround point, and the low currents typically found with multiple thymines. The nucleotides positioned near the center of the constriction were found to dominate the total current of a level, whereas the nucleotides to either side control the current to a lesser extent. This was consistent with previous MspA experiments where each current level was affected by ~four nucleotides in and around the constriction.

This and additional data indicated that a single-nucleotide influenced the current pattern for about four nucleotide steps through the nanopore. For example, a single-nucleotide substitution passing through MspA's constriction altered the current level pattern significantly, indicating that a nucleotide's identity and position in the strand was encoded in the observed current. This was consistent with the previously reported findings in Manrao et al. (2011) using a single-nucleotide polymorphism in NeutrAvidin-anchored DNA.

Also described in Manrao et al. (2012), the inventors demonstrated the feasibility of reading heterogeneous DNA with MspA and phi29 DNAP using four DNA heteromeric base sequences. Analogous to the block homopolymer DNA, these strands also had two abasic residues near the end of the template sequence to produce a clear marker signifying successful completion of synthesis. For each experimental sequence, consistent current patterns were obtained with distinct features corresponding to individual nucleotide steps as DNA passed through MspA's constriction. Current levels were extracted from 20 events (obtained from two different pores) that exhibited unzipping and synthesis action of the system. A consensus of a current level sequence was formed from multiple events. The events were aligned to the consensus using a Needleman-Wunsch algorithm and overlayed the aligned levels. Consistent with previous experiments, the current trace showed a symmetry about a level that corresponded to the nucleotides in MspA's constriction when the blocking oligomer was completely removed, demonstrating that current levels observed during unzipping are repeated in opposite time-order during synthesis. As the blocking oligomer used in this experiment was shorter (15 nt) than the length of the template to be read, the number of levels observed during unzipping was fewer than those observed during synthesis, and the abasic peak marking the end of the read was not observed during unzipping.

Ultimately, the inventors demonstrated that individual single-stranded DNA molecules traversing through the short and narrow constriction of MspA under the control of phi29 DNAP yielded distinct current levels that were related to the sequence of the nucleotides in MspA's constriction. Current patterns were associated with two distinct processes: the 5' leading-motion of the DNA template, which is consistent with the nearly monotonic unzipping of the blocking oligomer, and the 3' leading-motion, which is consistent with synthesis by phi29 DNAP. Motion during synthesis was faster than unzipping, and the levels associated with most single-nucleotide advances could be identified. The DNA nucleotides that passed twice through MspA's constriction—once during unzipping of the blocking oligomer and once during synthesis—yielded redundant current readings. Thus, the inventors have shown that the high nucleotide sensitivity of MspA combined with the translocation control of phi29 DNAP enables single-nucleotide discrimination of DNA passing through a nanopore.

The following is a description of an exemplary approach for generating a quadromer reference map for nanopore-based analysis of DNA.

For sequence analysis of unknown DNA (or other polymers), the patterns of current levels obtained from nanopore-based analysis systems, such as those described above for DNA, need to be related to a known sequence. As described, the observed current signals for each iterative movement of a nucleotide subunit were determined by a plurality of nucleotides residing at that time in the pore constriction zone. Thus, a model predicting the current pattern will be complex, and deconvolution of a current trace to extract the underlying sequence will require comparison to a library of current levels for all possible combinations of the plurality of sequences, such as 4-mer sequences in the system described above.

To efficiently generate such a reference library, the present inventors measured the 256 current values for all the possible DNA quadromers, thus resulting in the Quadromer Map (QM). To optimize generation of all possible DNA quadromer current signals, the inventors designed reference DNA molecules that contained all 256 possible quadromer patterns (=$4^4$ because there are four possible monomeric subunits at each of four positions in the quadromer) in the shortest possible DNA sequence. Specifically, a De Bruijn sequence was generated, resulting in a circular, or cyclical sequence with the shortest possible sequence because each quadromer appears only once. Briefly, the De Bruijn sequence B is represented by B(k, n), wherein k is the number of potential polymer subunit identities (i.e., size of the subunit alphabet) and n is the number of contiguous subunits reflecting, corresponding to, or determining the resolution of the nanopore system (i.e., length of the "word"). See, van Aardenne-Ehrenfest, T and de Bruijn, N G, 1951, "Circuits and trees in oriented linear graphs", Simon Stevin 28:203-217. This results in a circular reference sequence of only $k^n$ characters long. For DNA and RNA molecules, the number of potential canonical polymer subunits (i.e., size of the alphabet, or k) is 4. In the MspA nanopore systems described above the number of subunits that contribute to any one signal (i.e., length of the word, or n) is also 4. Various software packages exist to generate De Bruijn sequences. Of particular use was the De Bruijn Sequence Generator, by W. Owen Brimijoin, available at Matlab® Central website provided on the world wide web by The Mathworks, Inc. Thus, a De Bruijn sequence results in a reference polynucleotide molecule that is $k^n$ characters, i.e., 256 nucleotides, long. In a linearized form, the De Bruijn sequence results in a reference sequence that is only 259 (i.e., $k^n$+n−1, or 256+4-1) nucleotides long and contains all possible quadromers in a contiguous orientation. This is a major advance in efficiency compared to the standard approach of concatamerizing each potential nucleotide quadromer, which results in a reference polynucleotide of 1024 nucleotides (i.e., total possible sequences each with four nucleotides, represented by $k^n$×4).

With this approach, a circular or cyclical De Bruijn sequence was generated, as set forth herein as SEQ ID NO:1 with arbitrary start and end points. Because any oligonucleotide with the reference sequence must be drawn through the nanopore using the same mechanism as the analyte DNA polymer(s), the circular De Bruijn sequence design was linearized. Additionally, the linear reference sequence design with the De Bruijn sequence was separated into eight distinct segments, which were used as the design templates for synthesis of the reference oligonucleotide constructs. This segmentation was performed to further facilitate the translocation of the resulting reference oligonucleotide constructs through the MspA nanopore. The eight reference sequence segments, set forth herein as SEQ ID NOS:2-9, contain unique and exclusive portions of the full length reference sequence. These sequences are listed in the "Reference Domain" column of Table 1 in descending order.

Furthermore, each reference oligonucleotide construct was generated with an additional overlap sequence to assist continuity between the signals generated from each reference oligonucleotide construct and to provide that every possible quadromer was presented in a contiguous sequence. Specifically, each reference oligonucleotide construct also contain an additional five nucleotide sequence proximal to the 3' end of the reference sequence domain. The additional nucleotide sequence duplicated (or "overlapped with") the first five nucleotide sequence at the 5' end of the subsequent reference sequence segment, which appeared in a different reference oligonucleotide construct. These sequences are listed in the "Overlap Domain" column of Table 1.

Proximal the overlap domain sequence, each reference oligonucleotide construct contained an abasic site (i.e., a location or position along the deoxyribose backbone lacking a base). The abasic site, listed as an "N" in the "Marker Domain" column in Table 1, served to provide a clear and unambiguous reference point in the current trace generated by the passage of this nucleotide position through the nanopore.

TABLE 1

Sequences for the domains of eight reference DNA polymers that provide one De Bruijn reference sequence.

| Reference Domain | Overlap Domain | Marker Domain | Calibration Domain | SEQ ID NO: for Full Sequence |
|---|---|---|---|---|
| CTTTTCTTCCTCTCCCAAAAGAAATAAACAA | GGAAG | N | CCTTCCAAAAAAAA | 11 |
| GGAAGTAAGCAATGAATTAATCAACGAACTAA | CCAGA | N | CCTTCCAAAAAAAA | 12 |
| CCAGAGATAGACAGGGAGGTAGGCAGTGAGTT | AGTCA | N | CCTTCCAAAAAAAA | 13 |
| AGTCAGCGAGCTAGCCATATACATGGATGTAT | GCATT | N | CCTTCCAAAAAAAA | 14 |
| GCATTGATTTATTCATCGATCTATCCACACGG | ACGTA | N | CCTTCCAAAAAAAA | 15 |
| ACGTACGCACTGACTTACTCACCGACCTACCC | GGGGT | N | CCTTCCAAAAAAAA | 16 |
| GGGGTGGGCGGTTGGTCGGCTGGCCGTGTGCG | TTTGT | N | CCTTCCAAAAAAAA | 17 |
| TTTGTTCGTCTGTCCGCGCTTGCTCGCCTGCC | CTTTT | N | CCTTCCAAAAAAAA | 18 |

The sequences of the domains are presented in the order as they appear in the full length sequence from the 5' end to the 3' end. The designations for the full-length sequences are provided in the right-hand column.

Finally, each reference oligonucleotide construct contained a calibration sequence proximal to the marker domain and at the 3' end of full-length sequence. The calibration sequence, CCTTCCAAAAAAAA (set forth herein as SEQ ID NO:10) served to provide a recognizable pattern of high and low current patterns for each signal output trace. Because the recognizable pattern is known to possess the same sequence in every reference oligonucleotide, the remaining output signals in each trace can be calibrated to, or adjusted to match, the traces obtained from the other reference oligonucleotides. This calibration allows for normalization of signal variation obtained from different oligonucleotides that are due to variations in the assay conditions, such as salinity, temperature, viscosity, or the shape of the nanopore construction region. Furthermore, the calibration sequence can also be included in the analyte DNA and allows for rescaling the ion currents (or other conditions) to the same conditions as the reference oligonucleotide constructs.

While Table 1 separately lists the sequences of the distinct Reference, Overlap, Marker, and Calibration domains of the eight reference oligonucleotide constructs (i.e., reference polymers) in their respective domain columns, the complete sequences for the reference oligonucleotide constructs are set forth herein as SEQ ID NOS:11-18, as indicated in the right-hand column.

While illustrative embodiments have been illustrated and described, it will be appreciated that various changes can be made therein without departing from the spirit and scope of the invention.

The embodiments of the invention in which an exclusive property or privilege is claimed are defined as follows:

1. A nanopore system for sequencing an unknown polymer, the system comprising:
   (a) a nanopore positioned in a nonconductive barrier between a first conductive liquid medium and a second conductive liquid medium that are in liquid communication through the nanopore;
   (b) a voltage source configured to apply a voltage across the nonconductive barrier;
   (c) a data acquisition device configured to detect an ion current through the nanopore; and (d) one or more unknown polymers operative to pass through the nanopore of the nanopore system from the first conductive liquid medium to the second conductive liquid medium to generate an ion current level pattern; and (e) a reference map comprising ion current level signals generated from polymer subunit combinations of a 4 or more-mer sequence; and wherein comparing the ion current level in the unknown polymer to the reference map provides polymer sequence information.

2. The nanopore system of claim 1, wherein each polymer subunit of the 4 or more-mer sequence comprises 4 or more nucleotides, and wherein each nucleotide is one of 4 canonical nucleotides, and further, wherein each polymer subunit comprises a 3' end and a 5' positioned at the opposite end of the 3' end.

3. The nanopore system of claim 2, wherein the 4 or more nucleotides comprising one polymer subunit contribute to one ion current level signal.

4. The nanopore system of claim 1, wherein all possible polymer subunit combinations of a 4-mer sequence result in 256 different possible polymers subunits.

5. The nanopore system of claim 4, wherein the 256 combinations of possible polymer subunits contribute to 256 different ion current level signals.

6. The nanopore system of claim 5, wherein the reference map comprises 256 different ion current level signals representing the ion current level signal for each 4 subunit combination of all possible 4 subunit combinations in the 4-mer sequence.

7. The nanopore system of claim 1, wherein the reference map comprising ion current level signals generated for all possible combinations of a 4 or more-mer sequence is generated by a reference polymer comprising a plurality of contiguous polymer subunits.

8. The nanopore system of claim 7, wherein the reference polymer comprises all possible polymer subunits.

9. The nanopore system of claim 8, wherein the reference polymer sequence is a De Bruijn sequence B represented by B(k, n), wherein k is the number of potential polymer subunit identities, and wherein n is the number of contiguous polymer subunits that correspond to the resolution of the nanopore system.

10. The nanopore system of claim 9, wherein the De Bruijn sequence is generated by taking a Hamiltonian path of an n-dimensional graph over k subunit identities, taking a Eulerian cycle of a (n−1)-dimensional graph over k subunit identities, using finite fields analysis, or concatenating all possible Lyndon words whose length divides by n.

11. The nanopore system of claim 2, wherein each polymer subunit further comprises an additional nucleotide sequence proximal to the 3' end of each polymer subunit, wherein the 3' additional nucleotide sequence overlaps with the 5' nucleotide sequence located on the adjacent polymer subunit.

12. The nanopore system of claim 11, wherein the additional nucleotide sequence proximal to the 3' end of each polymer subunit consists of a 1-50 subunit polymer sequence matching the 5' end of the adjacent reference polymer subunit.

* * * * *